US008039270B2

(12) United States Patent
Dultz et al.

(10) Patent No.: US 8,039,270 B2
(45) Date of Patent: Oct. 18, 2011

(54) APPARATUS AND METHOD FOR PERFORMING LIGAND BINDING ASSAYS ON MICROARRAYS IN MULTIWELL PLATES (75) Inventors: Shane C Dultz, Westlake Village, CA (US); David Ralin, South Pasadena, CA (US)

(73) Assignee: Maven Technologies, LLC, Los Angeles, CA (US)

( * ) Notice: Subject to any disclaimer, the term of this patent is extended or adjusted under 35 U.S.C. 154(b) by 554 days.

(21) Appl. No.: 12/125,735

(22) Filed: May 22, 2008

(65) Prior Publication Data

US 2009/0290157 A1    Nov. 26, 2009

(51) Int. Cl.
*G01N 33/543* (2006.01)
(52) U.S. Cl. ..... 436/518; 422/401; 422/407; 435/288.4; 436/164; 436/527; 436/805; 436/809
(58) Field of Classification Search .................. None
See application file for complete search history.

(56) References Cited

U.S. PATENT DOCUMENTS

| | | |
|---|---|---|
| 1,637,141 A | 7/1927 | Cooper |
| 3,858,616 A | 1/1975 | Thiery et al. |
| 4,146,365 A | 3/1979 | Kay et al. |
| 4,238,565 A | 12/1980 | Hornby et al. |
| 4,256,834 A | 3/1981 | Zuk et al. |
| 4,508,832 A | 4/1985 | Carter et al. |
| 5,164,589 A | 11/1992 | Sjoedin |
| 5,225,164 A | 7/1993 | Astle |
| 5,229,833 A | 7/1993 | Stewart |
| 5,234,769 A | 8/1993 | Shevlin |
| 5,255,075 A | 10/1993 | Cush |
| 5,313,264 A | 5/1994 | Ivarsson et al. |
| 5,341,215 A | 8/1994 | Seher |
| 5,437,840 A | 8/1995 | King et al. |
| 5,446,534 A | 8/1995 | Goldman |
| 5,483,346 A | 1/1996 | Butzer |
| 5,485,277 A | 1/1996 | Foster |
| 5,491,097 A | 2/1996 | Ribi et al. |
| 5,491,556 A | 2/1996 | Stewart et al. |

(Continued)

FOREIGN PATENT DOCUMENTS

AU           742417           2/2000

(Continued)

OTHER PUBLICATIONS

Tadashi Saitoh, et al."Optical Characterization of Very Thin Hydrogenated Amorphous Silicon Films Using Spectroscopic Ellipsometry"; Japanese Journal of Applied Physics; vol. 30, No. 11B, Nov. 1991. pp. L1914-L1916.

(Continued)

*Primary Examiner* — Chris L Chin
(74) *Attorney, Agent, or Firm* — Haynes and Boone, LLP (57) ABSTRACT Ellipsometry systems for imaging binding events between analytes in a sample and an array of ligands in an evanescent field generated by a beam of light reflected from the plane of the ligands is adapted to a multiwell plate structure in common use. In one example, a film of prism arrays is affixed to the underside of the plate with each prism array located in registry with a well and ligand arrays being immobilized on the (planar) bottom surface of the wells. The prism array may be formed in a film and juxtaposed with the bottom surface of the plate or a prism array can be made integral with the plate bottom of a multiwell plate.

20 Claims, 7 Drawing Sheets

U.S. PATENT DOCUMENTS

| | | | |
|---|---|---|---|
| 5,573,956 | A | 11/1996 | Hanning |
| 5,593,130 | A | 1/1997 | Hansson et al. |
| 5,633,724 | A | 5/1997 | King et al. |
| 5,641,640 | A | 6/1997 | Hanning |
| RE35,716 | E | 1/1998 | Stapleton et al. |
| 5,738,825 | A | 4/1998 | Rudigier et al. |
| 5,753,518 | A | 5/1998 | Karlsson |
| 5,796,858 | A | 8/1998 | Zhou et al. |
| 5,813,439 | A | 9/1998 | Herrero et al. |
| 5,856,873 | A | 1/1999 | Naya et al. |
| 5,922,594 | A | 7/1999 | Loefas |
| 5,922,604 | A | 7/1999 | Stapleton et al. |
| 5,955,729 | A | 9/1999 | Nelson et al. |
| 5,965,456 | A | 10/1999 | Malmqvist et al. |
| 5,972,612 | A | 10/1999 | Malmqvist et al. |
| 6,008,010 | A | 12/1999 | Greenberger et al. |
| 6,008,893 | A | 12/1999 | Roos et al. |
| 6,026,053 | A | 2/2000 | Satorius |
| 6,045,996 | A | 4/2000 | Cronin et al. |
| 6,065,501 | A | 5/2000 | Feret et al. |
| 6,127,183 | A | 10/2000 | Ivarsson et al. |
| 6,140,044 | A | 10/2000 | Bessemer et al. |
| 6,143,513 | A | 11/2000 | Loefas |
| 6,143,574 | A | 11/2000 | Karlsson et al. |
| 6,197,595 | B1 | 3/2001 | Anderson et al. |
| 6,200,814 | B1 | 3/2001 | Malmqvist et al. |
| 6,207,381 | B1 | 3/2001 | Larsson et al. |
| 6,253,793 | B1 | 7/2001 | Dupoiron et al. |
| 6,277,330 | B1 | 8/2001 | Liu et al. |
| 6,289,286 | B1 | 9/2001 | Andersson et al. |
| 6,354,333 | B1 | 3/2002 | Dupoiron et al. |
| 6,355,429 | B1 | 3/2002 | Nygren et al. |
| 6,415,725 | B1 | 7/2002 | Yoshikazu |
| 6,475,809 | B1 | 11/2002 | Wagner et al. |
| 6,493,097 | B1 | 12/2002 | Ivarsson |
| 6,503,760 | B2 | 1/2003 | Malmqvist et al. |
| D472,644 | S | 4/2003 | Dawson et al. |
| 6,549,011 | B2 | 4/2003 | Flatt |
| 6,589,798 | B1 | 7/2003 | Loefas |
| 6,594,011 | B1 | 7/2003 | Kempen |
| D480,149 | S | 9/2003 | Dawson et al. |
| 6,698,454 | B2 | 3/2004 | Sjoelander et al. |
| 6,710,870 | B1 | 3/2004 | Marowsky et al. |
| 6,714,303 | B2 | 3/2004 | Ivarsson |
| 6,806,051 | B2 | 10/2004 | Ellson |
| 6,810,286 | B2 | 10/2004 | Donovan et al. |
| 6,833,920 | B2 | 12/2004 | Rassman et al. |
| 6,859,280 | B2 | 2/2005 | Kempen |
| 6,882,420 | B2 | 4/2005 | Rassman et al. |
| 6,981,526 | B2 | 1/2006 | Glejbol et al. |
| 7,045,287 | B2 | 5/2006 | Smith et al. |
| 7,193,711 | B2 | 3/2007 | Rassman et al. |
| 7,195,872 | B2 | 3/2007 | Agrawal et al. |
| 7,233,391 | B2 * | 6/2007 | Schermer et al. ............ 356/246 |
| 2002/0019019 | A1 | 2/2002 | Hamalainen et al. |
| 2002/0021443 | A1 | 2/2002 | Venkatasubbarao et al. |
| 2002/0154311 | A1 | 10/2002 | Ivarsson |
| 2002/0182717 | A1 | 12/2002 | Karlsson |
| 2003/0022388 | A1 | 1/2003 | Roos et al. |
| 2003/0067612 | A1 | 4/2003 | Ivarsson |
| 2003/0112432 | A1 | 6/2003 | Yguerabide et al. |
| 2003/0148401 | A1 | 8/2003 | Agrawal et al. |
| 2003/0175160 | A1 | 9/2003 | Archibald et al. |
| 2003/0205681 | A1 | 11/2003 | Modlin |
| 2003/0232384 | A1 | 12/2003 | Kocher et al. |
| 2004/0002167 | A1 | 1/2004 | Andersson et al. |
| 2004/0012676 | A1 | 1/2004 | Weiner et al. |
| 2004/0023247 | A1 | 2/2004 | Xu et al. |
| 2004/0030504 | A1 | 2/2004 | Helt et al. |
| 2004/0038268 | A1 | 2/2004 | Pirrung et al. |
| 2005/0105091 | A1 | 5/2005 | Lieberman et al. |
| 2005/0110989 | A1 | 5/2005 | Schermer et al. |
| 2005/0148063 | A1 | 7/2005 | Cracauer et al. |
| 2007/0159629 | A1 | 7/2007 | Eing et al. |
| 2007/0178012 | A1 * | 8/2007 | Ferrante et al. ............ 422/82.05 |

FOREIGN PATENT DOCUMENTS

| | | |
|---|---|---|
| WO | WO 8911057 | 11/1989 |
| WO | WO 9100467 | 1/1991 |
| WO | WO 96/08720 | 3/1996 |
| WO | WO 96/38729 | 12/1996 |
| WO | WO 97/19375 | 5/1997 |
| WO | WO 98/32002 | 7/1998 |
| WO | WO 03/056337 A1 | 7/2003 |
| WO | WO 03/102580 A1 | 12/2003 |

OTHER PUBLICATIONS

"Handbook of Optics", Michael Bass Editor in Chief, by The Optical Society of America; vol. 1; pp. 4.23, 4.24; 1995 McGraw-Hill, Inc.

Bass, et al. "Handbook of Optics", by The Optical Society of America; vol. 1; Section 41.10; 1995 McGraw-Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930-2936, Aug. 1996.

Max Born et al. "Principles of Optics—Electromagnetic Theory of Propagation, Interference and Diffraction of Light", Sixth Edition, pp. 47-51 Pergamon Press.

Eggins, "Biosensors: An Introduction", pp. 112-113, 1987 John Wiley & Sons.

Danny Van Noort et al. "Monitoring Specific Interaction of Low Molecular Weight Biomolecules on Oxidized Porous Silicon Using Ellipsometry", Biosensors & Bioelectronics vol. 13, No. 3-4 pp. 439-449, 1998 Elsevier Science, S.A. Great Britain.

Gang Jin et al. "Imaging Ellipsometry for Biosensor Applications" Transducers '95. Eurosensors IX, Digest of Technical Papers vol. 2, Sessions A7-D13, Papers No. 232-496 pp. 509-512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44-50, 1992.

Ulf Jonsson et al. "Flow-Injection Ellipsometry—An in Situ Method for the Study of Biomolecular Adsorption and Interaction at Solid Surfaces," Colloids and Surfaces, 13 (1985) pp. 333-339, 1985 Elsevier Science Publishers BV, Amsterdam, The Netherlands.

Jonsson, Ulf et al. "Biosensors Based on Surface Concentration Measuring Devices—The Concept of Surface Concentration" Progress in Colloid and Polymer Sci. vol. 70, pp. 96-100, 1985.

Schena, Mark "DNA Microarrays: A Practical Approach" Edited by Mark Schena, Department of Biochemistry, Beckman Center, Stanford University Medical Center, Stanford, USA, Oxford University Press, 1999.

Schema, PhD. Mark, "Microarray Biochip Technology" TeleChem International, Inc., Sunnyvale, California, USA, A BioTechniques Books Publication, Eaton Publishing, pp. 10-11, 2000.

Harland G. Tompkins, et al. "Spectroscopic Ellipsometry and Reflectometry A User's Guide" A Wiley-Interscience Publication, John Wiley & Sons, Inc., 1999.

Ulf Jonsson et al. "Surface Immobilization Techniques in Combination with Ellipsometry" Methods in Enzymology vol. 137, Immobilized Enzymes and Cells Part D pp. 381-1351, 1988 Academic Press, Inc. Harcourt Brace Jovanovich, Publishers.

Ch Striebel et al. "Characterization of Biomembranes by Spectral Ellipsometry, Surface Plasmon Resonance and Interferometry with Regard to Biosensor Application", Biosensors & Bioelectronics 9, pp. 139-146, 1994 Elsevier Science Publishers Ltd.

T.A. Ruzgas et al. "Ellipsometric Immunosensors for the Determination of γ-Interferon and Human Serum Albumin", Biosensors & Bioelectronics 7, pp. 305-308, 1992 Elsevier Science Publishers Ltd.

Haken Nygren et al. "Determination by Ellipsometry of the Affinity of Monoclonal Antibodies", Journal of Immunological Methods, 92, pp. 219-225, 1986 Elsevier Science Publishers Ltd.

John F. Place et al. "Opto-electronic Immunosensors: A Review of Optical Immunoassay At Continuous Surfaces", Biosensors 1, pp. 321-353, 1985 Elsevier Applied Science Publishers Ltd., England.

A. Brecht et al. "Biosensors: Fundamentals, Technologies and Applications" GBF Monographs, vol. 17, pp. 174-178, 1991 Germany.

Hakan Nygren et al. "Kinetics of Antibody-Binding to Surface-Immobilized Antigen: Influence of Mass Transport on the Enzyme-Linked Immunosorbent Assay (ELISA)", Journal of Colloid and Interface Science, vol. 107, No. 2 pp. 560-566, Oct. 1985 Academic Press, Inc.

Martin Malmsten et al. "Effects of Hydrophilization and Immobilization on the Interfacial Behavior of Immunoglobulins", Journal of Colloid and Interface Sicence 177, pp. 70-78, 1996 Academic Press, Inc.

Pentti Tengvall et al. "Temporal Studies on the Deposition of Complement on Human Colostrum IgA and Serum Immobilized on Methylated Silicon", Journal of Biomedical Materials Research, vol. 35, pp. 81-91, 1997 John Wiley & Sons, Inc.

Huaiyou Wang et al. "Assembly of Antibodies in Lipid Membranes for Biosensor Development", Applied Biochemistry and Biotechnology, vol. 53 pp. 163-181, 1995 Humana Press Inc.

G. Elender et al. "Wetting and Dewetting of Si/SiO2-Wafers by Free and Lipid-Monolayer Covered Aqueous Solutions Under Controlled Humidity", Journal de Physique, II France 4 pp. 455-479, Mar. 1994.

C.F. Mandenius et al. "Coupling of Biomolecules to Silicon Surfaces for use in ellipsometry and other related techniques", Methods in Enzymology, vol. 137, pp. 389-394, 1988 Academic Press, Inc.

A.W. Flounders et al. "Patterning of immobilized antibody layers via photolithography and oxygen plasma exposure", Biosensors and Bioelectronics, vol. 12, No. 6 pp. 447-456, 1997 Elsevier Science Ltd., Great Britain.

A. Ahluwalia et al. "A comparative study of protein immobilization techniques for optical immunosensors", Biosensors and Bioelectronics 7, (1991) pp. 207-214, 1992 Elsevier Science Publishers Ltd.

Dr. Rudolf Oldenbourg "Metamorph Imaging System", http://www.image1.com/products/metapolscope/ Universal Imaging Corporation Last Updated Jun. 10, 1999 pp. 1-2.

Dr. Rudolf Oldenbourg "A new view on polarization microscopy", Nature, vol. 381, pp. 811-812, Jun. 27, 1996.

Clifford C. Hoyt et al. "Structural analysis with quantitative birefringence imaging", American Laboratory, pp. 34-42, Jul. 1999.

Dirk Honig et al. "Direct visualization of monolayers at the air-water interface by Brewster angle microscopy", J. Phys. Chem., pp. 4590 & 4592, 1991 American Chemical Society.

S. Henon et al. "Microscope at the Brewster angle: direct observation of first-order phase transitions in monolayers", Rev. Sci. Instrum. 62, (4) pp. 936-939, Apr. 1991 American Institute of Physics.

Gang Jin et al. "A biosensor concept based on imaging ellipsometry for visualization of biomolecular interactions", Analytical Biochemistry 232, pp. 69-72, 1995.

Pentti Tengvall et al. "Complement activation by 3-mercapto-1,2-propanediol immobilized on gold surfaces", Biomaterials vol. 17, No. 10 pp. 1001-1007, 1995 Elseviar Science Ltd., Great Britain.

H. Arwin "Spectroscopic ellipsometry and biology: recent developments and challenges", Thin Solid Films 313-314, pp. 7640774, 1998 Elsevier Science S.A.

Christopher Palmer "Diffraction Grating Handbook", pp. 35-44, 2000 Richardson Grating Laboratory, Rochester, New York.

Erwin G. Loewen "Diffraction Gratings, Ruled and Holographic", Applied Optics and Optical Engineering, vol. IX, pp. 33-71, Bausch and Lomb, Inc., Rochester, New York 1983 Academic Press, Inc.

Willems, Goerge M., et al., Adsorption and Conversion of Prothrombin on a Rotating Disc, Blood, Jul. 15, 1993, vol. 82, No. 2, pp. 497-504.

U.S. Appl. No. 11/677,674, Dultz et al.
U.S. Appl. No. 11/748,023, Dultz et al.
U.S. Appl. No. 11/696,369, Dultz.
U.S. Appl. No. 11/752,056, Dultz.
U.S. Appl. No. 12/125,685, Dultz.
U.S. Appl. No. 12/650,327, Dultz et al.

PCT Written Opinion of the International Searching Authority, Nov. 23, 2010, 8 pages, The International Bureau of WIPO.

* cited by examiner

APPARATUS AND METHOD FOR PERFORMING LIGAND BINDING ASSAYS ON MICROARRAYS IN MULTIWELL PLATES

CROSS-REFERENCE TO RELATED APPLICATIONS

This application is related to pending U.S. application Ser. No. 11/677,674, filed Feb. 22, 2007, pending U.S. application Ser. No. 11/748,023, filed May 14, 2007, pending U.S. application Ser. No. 11/696,369, filed Apr. 4, 2007, and pending U.S. application Ser. No. 11/752,056, filed May 22, 2007, the contents of which are incorporated by reference herein for all purposes.

FIELD OF THE INVENTION

This invention relates to an apparatus for characterizing molecular binding events when performing ligand binding assays and more particularly to such systems employing ligand spots or microarrays in a multiwell, integrated optics format.

BACKGROUND

U.S. Pat. No. 6,594,011 issued Jul. 15, 2003, the entirety of which is incorporated by reference herein for all purposes, discloses an imaging apparatus and method for real time imaging ellipsometry for high throughput sensing of binding events useful in molecular interaction analysis including biotech applications. The apparatus disclosed employs the immobilization of an array of binding or capture molecules ("ligands") on a planar surface of a transparent substrate and the use of a beam of polarized light directed at the underside of the surface in a manner to achieve total internal reflection (TIR) and generate an evanescent field in the plane of the ligands. The ligands are exposed to a biological sample and analytes in the biological sample bind to different patterns of the immobilized ligands in a manner to change the polarization at locations in the array at which binding occurs. An image of the array is compared with a stored image of the initial light polarization shifts to determine the location and magnitude of binding events within the array, thus identifying and quantitating the analytes present in the biological sample.

The apparatus for implementing the foregoing technique employs a prism or gratings to achieve the requisite TIR generated evanescent field, the prism being the most practical implementation for imaging applications.

TIR imaging ellipsometry works well for fields of view up to 1-2 $cm^2$, which permits real time imaging of tens of thousands of binding events simultaneously. However, there is a need to be able to image or scan areas which are much larger, such as 128 mm×86 mm (e.g., the area of both 384 well and 96 well plates) to permit lower costs per test and for multiple tests per patient for large numbers of patients simultaneously, which is increasingly a requirement for clinical diagnostics and personalized medicine. Simply scaling up the prism geometry so that the field of view covers an entire 1536 well, 384 well or 96 well plate has the following practical and technical drawbacks. In addition to the high expense of large optics, image quality becomes more challenging to maintain as the field of view is increased. Spherical aberration effects, optical path-length and depth of field issues demand much more space in order to keep the quantitative imaging errors low. Additionally, because the optics are too expensive and bulky to be part of the disposable plate, the optical coupling to the disposable plate is done by the user and in many applications, this is not practical, especially when high throughput is required. Obviating the need for a prism simplifies both the instrument and interface between the instrument and disposable multiwell plate.

SUMMARY

The present invention provides an advantageous apparatus, system, and method for performing ligand binding assays using microarrays in a multiwell plate format. The invention is based on the realization that the aforementioned imaging ellipsometer system could be adapted to the familiar multiwell plate by positioning an array of mini-prisms on the underside of a multiwell plate, to eliminate the need for a user to manually or otherwise optically couple prisms to the bottom of the disposable plate as has been previously required. The present invention provides for a completely integrated, low cost disposable plate where ligand arrays can be printed on the inside bottom of the individual wells of a multiwell plate, which then allows a beam of polarized light to be directed through a prism film attached to the external plate bottom to achieve TIR and an evanescent field in the plane of the ligands. In one embodiment, each prism of a prism array is in registry with a well. For a standard ninety-six well plate, for example, an array of ninety-six prisms are attached to the plate underside with each prism in registry with a corresponding well.

In one embodiment, in accordance with this invention, a single continuous sheet of prisms is located on the underside of a glass bottom microwell plate where individual prisms are parallel to either rows or columns of wells in the plate, and the bottom surface of each well illustratively is planar and an array of ligands is immobilized on that planar inside bottom surface. Light, directed into a mini-prism array corresponding to a selected well or wells in a manner to achieve total internal reflection, generates an evanescent field in the plane of the array of ligands there and captures in the reflected light, an image of binding events between analytes in a sample in the well and the ligands immobilized on the well bottom surface. The image so captured is compared to an initialized image in a manner explained in the above-identified patent application and which is now well understood in the art.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 6 is a schematic representation of a portion of a multiwell plate in relation to the illumination, sensing and imaging subassemblies of the system; and Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

Prior to describing embodiments of the present invention in greater detail, the following definition is provided for use throughout the present document.

DEFINITIONS

Convex Figure: A figure is convex if every line segment drawn between any two points inside the figure lies entirely inside the figure. This definition is more general than the definition of a polygon since the edges of the figure can be curved.

Figure 1:
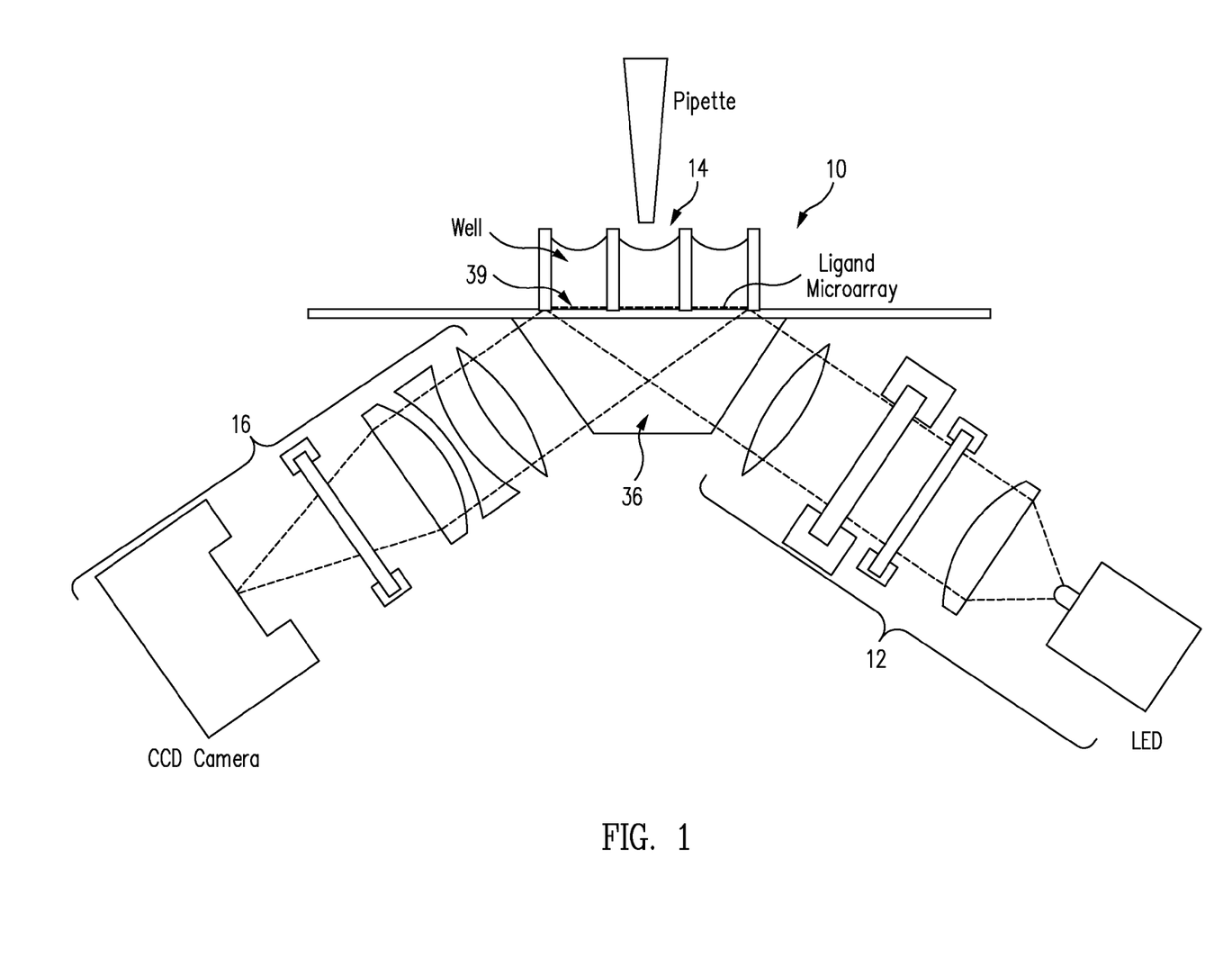
FIG. 1 is a schematic diagram of an imaging ellipsometry system disclosed in the above-identified patent.

FIG. 1 is a schematic diagram of an imaging ellipsometry system 10 as disclosed in the above identified patent. The system comprises three subassemblies: the illumination subassembly 12, the sensing subassembly 14, and the imaging subassembly 16. Each subassembly is described in greater detail in the above-identified patent and repeated discussion of the various components of those subassemblies is not necessary for an understanding of the invention. Suffice it to say that light is supplied by subassembly 12, directed into prism 36 and totally internally reflected (TIR) from surface 39 into the imaging subassembly 16. Importantly, light reflected from surface 39 produces an evanescent field at that surface and as previously noted herein, an array of ligands is immobilized on the TIR surface for exposure to a sample for testing for the presence of analytes in the sample.

The recognition that an individual well bottom surface of a familiar multiwell plate can be adapted for the placement of an immobilized ligands array pattern which could be imaged through a prism array on the underside of the plate in registry with the well is considered a significant contribution in the art. Such an adaptation also allows for an array of truncated mini prisms, each prism of the array located to achieve a miniaturized system of the type shown in FIG. 1. Such an arrangement allows for a significant increase in the number of tests which can be carried out with the apparatus.

Optimized low birefringent plastic prism arrays are easily and inexpensively produced and thus not only avoids the high cost of an individual glass prism per well, with the arduous application of index matching liquid, but also avoids the problem of unwanted birefringent problems normally encountered if the prism is formed of most injection molded plastics.

Figure 2A:
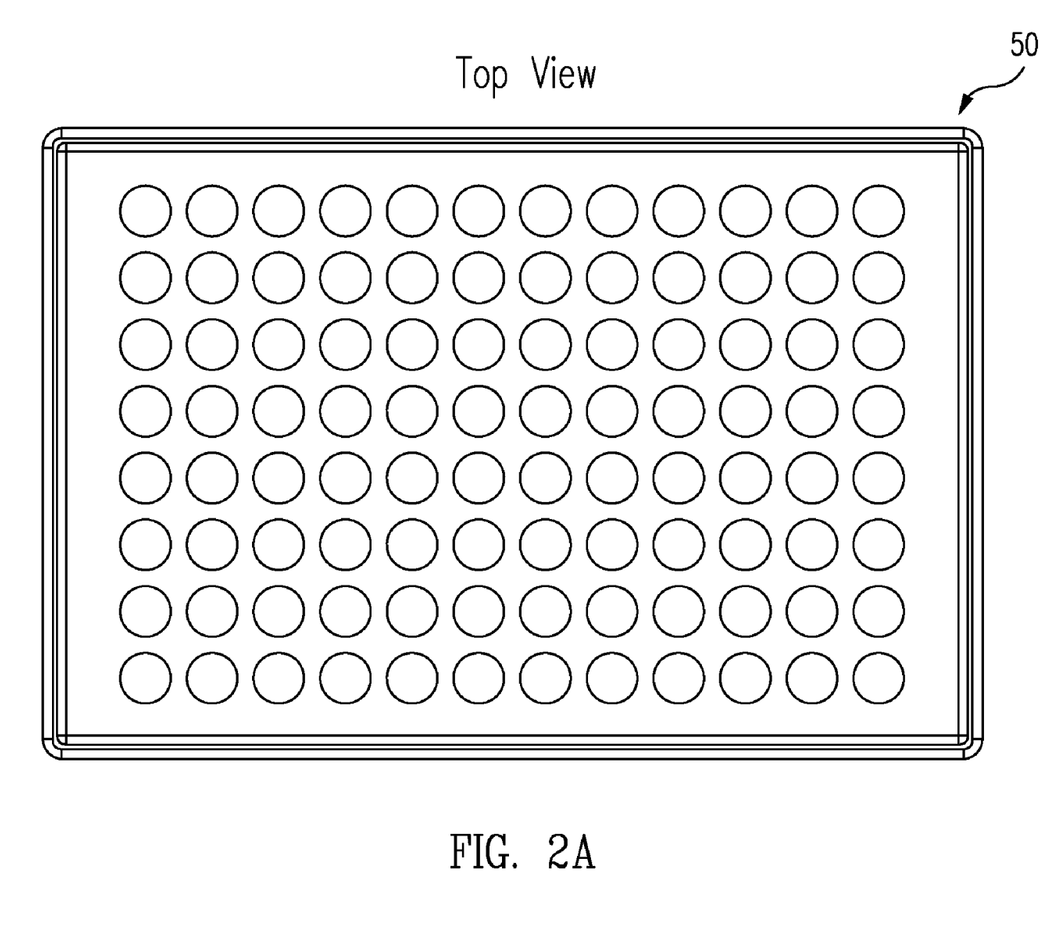
FIG. 2A is a top schematic view of a multiwell plate adaptable in accordance with the principles of this investigation.
Figure 2B:
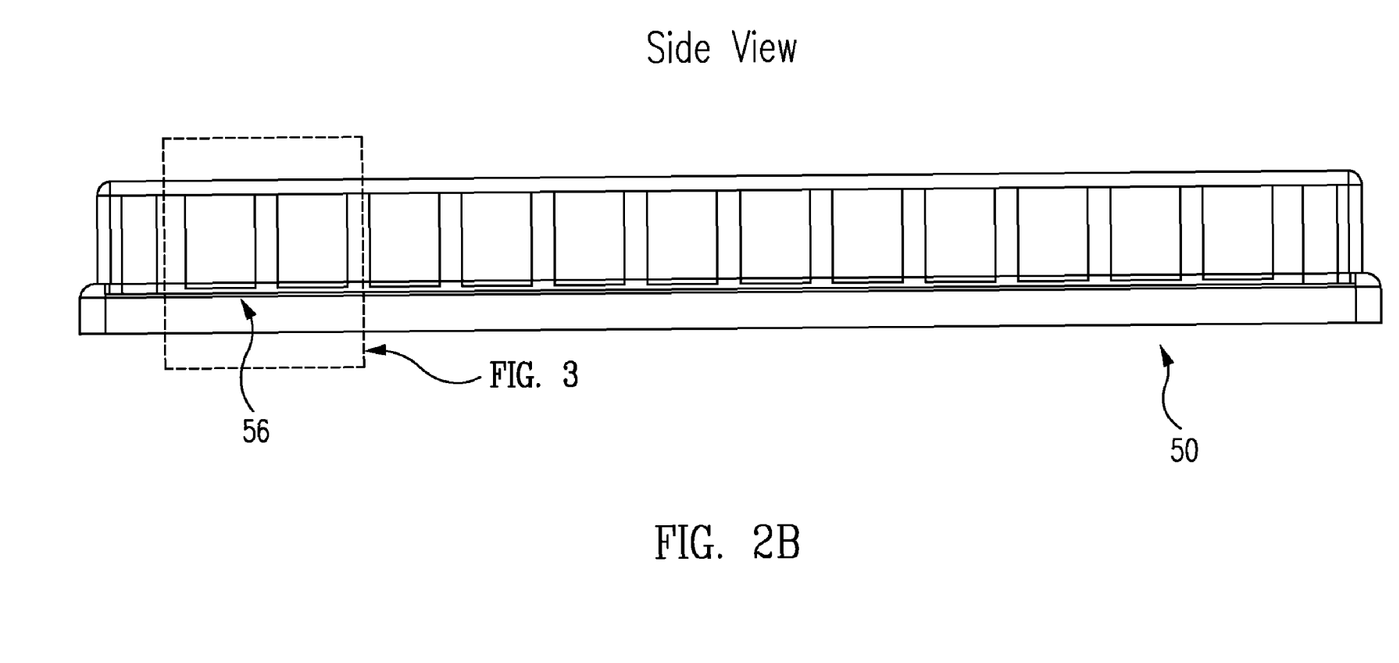
FIG. 2B is a schematic side view of a multiwell plate illustrating the location of a prism array film with respect to the wells of the plate.
Figure 3:
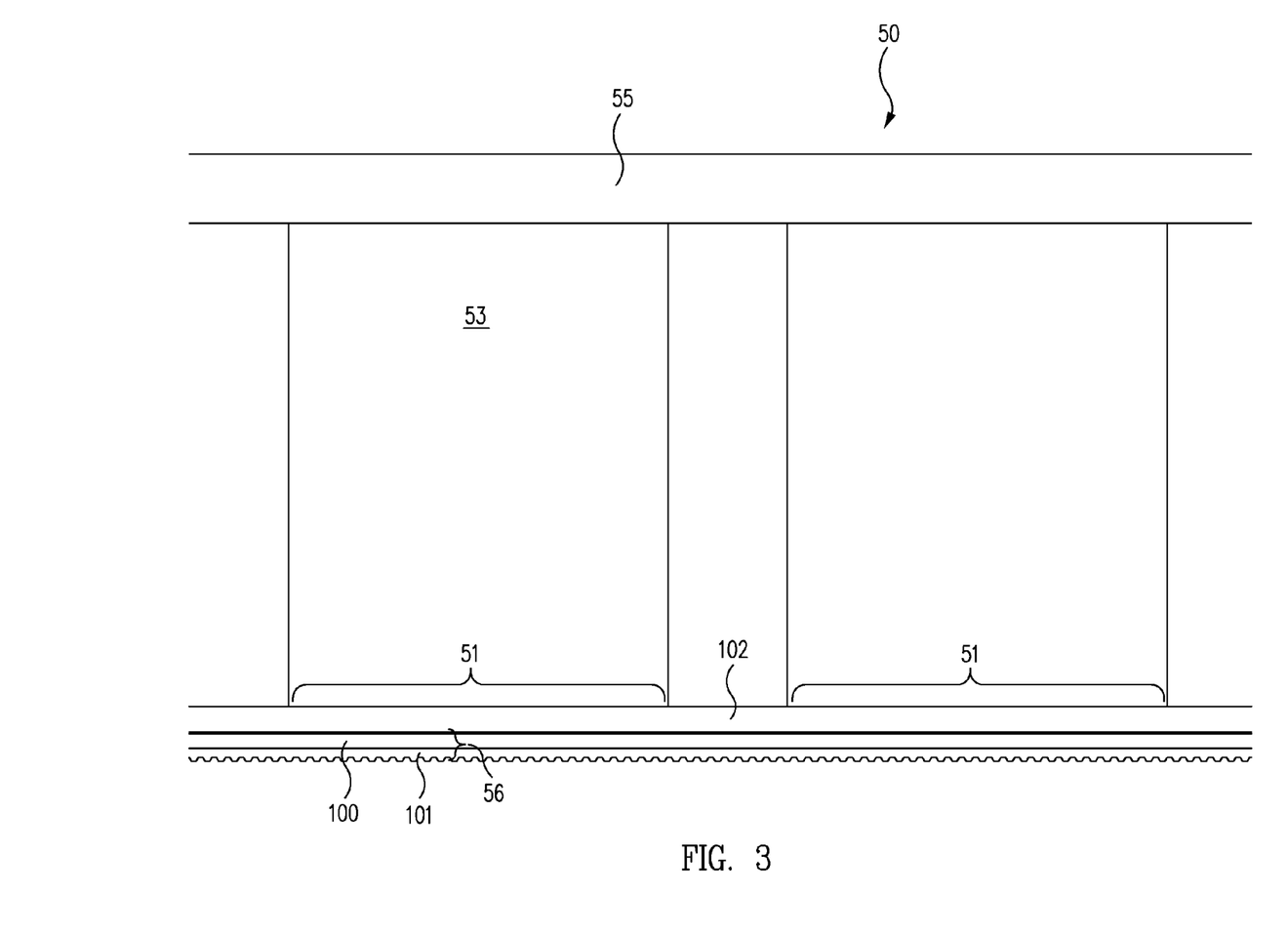
FIG. 3 is a side view of an enlarged portion of the multiwell plate shown in FIGS. 2A and 2B showing the prism array film.

FIGS. 2A and 2B show top and side views of a multiwell plate 50 adapted for providing an array of miniaturized ellipsometer imaging systems in accordance with the principles of this invention. Specifically, FIG. 2A is a top view of an illustrative ninety-six well plate 50, and FIG. 2B illustrates a side view of plate 50 including a substrate (e.g., a substrate 102 shown in FIG. 3) and a prism array 56 optically coupled underneath the substrate. FIG. 3 is a side view of an enlarged portion of the multiwell plate shown in FIGS. 2A and 2B showing the prism array 56, in one embodiment formed of a sheet 100 and a prism film 101. The plate has dimensions of 8.6 cm by 12.8 cm, in one example, corresponding to the dimensions of commercially available multiwell plates. The side and enlarged views of FIGS. 2B and 3, respectively, show the planar well bottoms for the wells, each of which planar well bottom provides the requisite planar surface for a ligand array to be immobilized. A mini-prism array 56 is attached to the underside of plate 50 (e.g., under substrate 102) in accordance with the principles of this invention. Prism array 56 may comprise a uniform pattern of prisms or a pattern of film arrays spaced apart to correspond to the positions of wells in a multiwell plate.

Figure 4:
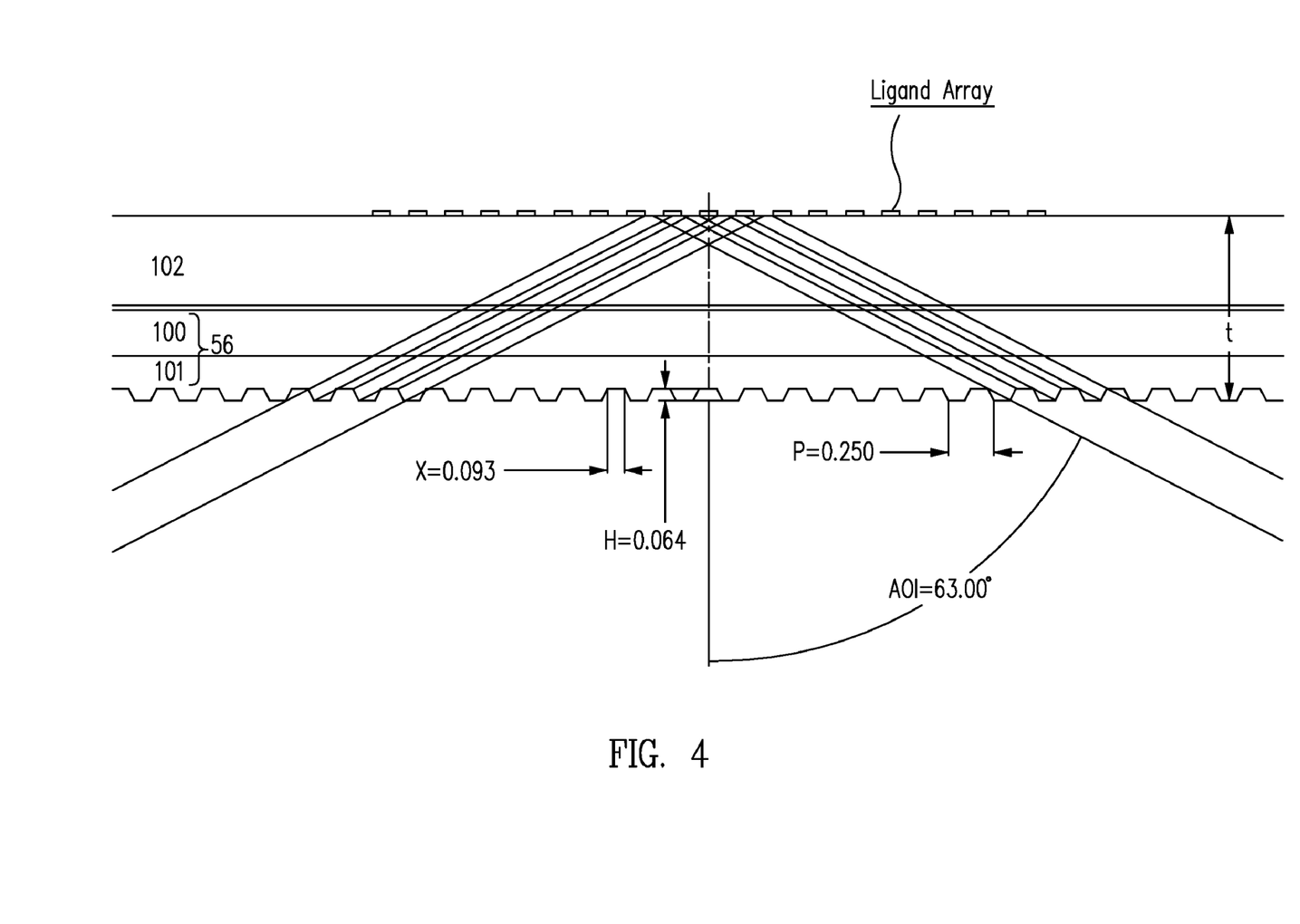
FIG. 4 is an enlarged schematic side view of a prism array bonded to an example glass substrate, illustrating an example of the geometry and dimensions of the prisms and the portion of the light beam which is transmitted through the structure.

Referring now to FIG. 4 in conjunction with FIGS. 2A-2B and 3, the prisms of the prism array 56 are shown to have a truncated geometry and are spaced apart from one another. The prism geometry, spacing between prisms, the prism index of refraction and the placement of the prism are all important aspects of this invention.

In order for neighboring prisms not to "shadow" or block the light source from entering the planar prism faces, there are certain constraints on the geometry of the prism film structure. Examples of the height "H" and pitch "P" of the prisms are shown in FIG. 4 as well as the angle of incidence (AOI) of the light beam. For the case where light enters and exits normal to the faces of the individual prism rows the following geometric constraints exist for the maximum height of the prisms.

$$h \leq \frac{P\cot(\theta)}{2} \quad \text{(Equation 1)}$$

where P is the prism pitch and θ is the AOI of the light beam. The distance "X" between adjacent prisms is determined by $$x \geq \frac{P(1 - \cot^2(\theta))}{2} \quad \text{(Equation 2)}$$

FIG. 4 shows an example using a prism pitch P=250 μm and an angle of incidence θ=63.0° which is the appropriate angle of incidence if the prism film has a refractive index of 1.52 and the light is to undergo total internal reflection from an aqueous sample. The geometric constraints indicate for the prism pitch that the height of the prisms should be no larger than 63.7 μm or that the distance between prisms should be at least 92.5 μm so that individual prism faces are not shadowed. These constraints are guides in the manufacturing of the prisms with minimal transmission birefringence characteristics and which maximize the amount of light which is transmitted into the prism film structure from air. For larger prism structures, another constraint exists on the total distance "t" between the base of the prisms and the ligand array (FIG. 4) in order to maximize the amount of light which also exits the prism film via the angled prism faces rather than the horizontal faces which block the exiting light. Given the same trapezoidal geometry, the following equation gives the total thickness values which achieve maximum total transmission:

$$t = \frac{nP\cot(\theta)}{2} \quad \text{(Equation 3)}$$
$$= nh \text{ where } n \text{ is any integer, 1, 2, 3, ...}$$

This means that the glass thickness and prism film thickness should be chosen to meet this requirement in the general case. For the example here, the thickness difference between the maximum and minimum amount of light throughput is only ~30 μm. Besides the difficulty in achieving these low tolerances when the glass substrate may be as thick as 1 mm, equation 3 does not take into account light diffraction which will decrease the thickness dependence with smaller and smaller prisms.

The prism pitch P is scalable from at least the micron scale to the centimeter scale where critical alignment requirements of the prisms only occur when the prism pitch approaches the spot to spot spacing in the ligand array (typically on the order of 0.1 mm). As the individual prisms become much smaller, alignment becomes less critical with the tradeoff that diffraction effects become more critical.

Referring to FIGS. 3 and 4 in particular, the prism array may, in accordance with the principles of this invention, be formed directly as an integrated portion of the multiwell plate bottom. In embodiments of this type, a substrate (e.g., substrate 102) is made in the form of a flat slide-like slab formed by rolling, for example, a plastic into a negative mold and printing ligand arrays on island areas 51 on the top surface of the resulting substrate 102. The substrate is then juxtaposed with a plastic top member 55 which has through apertures 53 corresponding to the island areas 51, thus forming the wells resulting in a plate 50 as shown in FIG. 3. Top member 55 includes openings in the cover above each aperture 53 to allow for the introduction of samples.

The prism arrays may be embossed, stamped or rolled from a continuous layer of UV-curable monomer or polymer of which Cyclic Olefin Copolymer (COC), Cyclic Olefin Polymer (COP), polyester, acrylic, polycarbonate, polystyrene, polypropylene or optical quality resins are examples. In such a case, the resulting prism film can have a thickness in the range of about 0.075-0.75 mm in one example. The prism array is bonded to the plate underside with an index matching adhesive so that the prisms act to couple the incident light of the imaging system into the transparent material (glass or plastic) which forms the bottom of the wells so that total internal reflection can occur at the plane where ligand arrays reside. The prism array is fabricated from high optical quality material and is processed in a manner to have a total birefringence of less than $1 \times 10^{-5}$.

The prism array may also be created by rolling a plastic in liquid form over a negative mold. This prism film could be a dielectric with excellent optical properties which hardens by UV-curing or other catalytic curing process. In one particular embodiment, the prism film itself can be made from a metal silicon or ceramic master mold or pattern onto which a UV-curing low-birefringence material is poured or rolled and cured. Prism arrays can be hot embossed in a suitable, transparent layer of, for example, plastic polymer which has an index of refraction between 1.46 and 1.59 selected to match the index of the ligand array support on which the wells are formed.

In a specific embodiment of this invention, a UV-curable, low birefringence polymer was poured into a metal master. A nominally planar sheet 100 of carrier material with selected optical and mechanical properties (FIG. 4) was plasma treated on one or both sides to improve bonding characteristics and positioned in contact with uncured polymer forming a prism film 101. The polymer was exposed to UV light to initiate curing. Ligand arrays, in one embodiment were immobilized directly on the surface of substrate 102 (e.g., formed of glass). Sheet 100 (already bonded to the prism film 101) and substrate 102 were bound together by an indexing matching adhesive. The well configuration was achieved by attaching to the top surface of substrate 102 (on which the ligand arrays are immobilized) a plastic, rigid top member 55 with apertures 53 (FIG. 3) to encompass the ligand arrays thus forming the wells for analytic samples. The prism height, spacing, width and slope dimensions were smaller than shown in FIG. 4 and did not satisfy the geometric constraints of equations 1 and 2 but nonetheless, produced results which allowed imaging of protein microarray spots.

Embodiments using metal and silicon master patterns have also been tested using UV curable, low-birefringence polymer for the prism film with prism film thicknesses of between 40 and 1000 microns. Carrier sheets (e.g., sheet 100 of FIG. 4) were formed using materials such as COC and COP (cyclic olefin copolymer and polymer).

While the invention is described in terms of specific embodiments, other embodiments could readily be adapted by one skilled in the art. For example, prism array 56 is not limited to being formed of a carrier sheet 100 bonded to a prism film 101 and may instead be formed without a carrier sheet, which is optional. Furthermore, prism array 56 is not necessarily bonded underneath a substrate 102 but instead may bond directly to a top member 55 to form a multiwell plate, and ligands may be directly placed on a top surface of the prism array.

Figure 5:
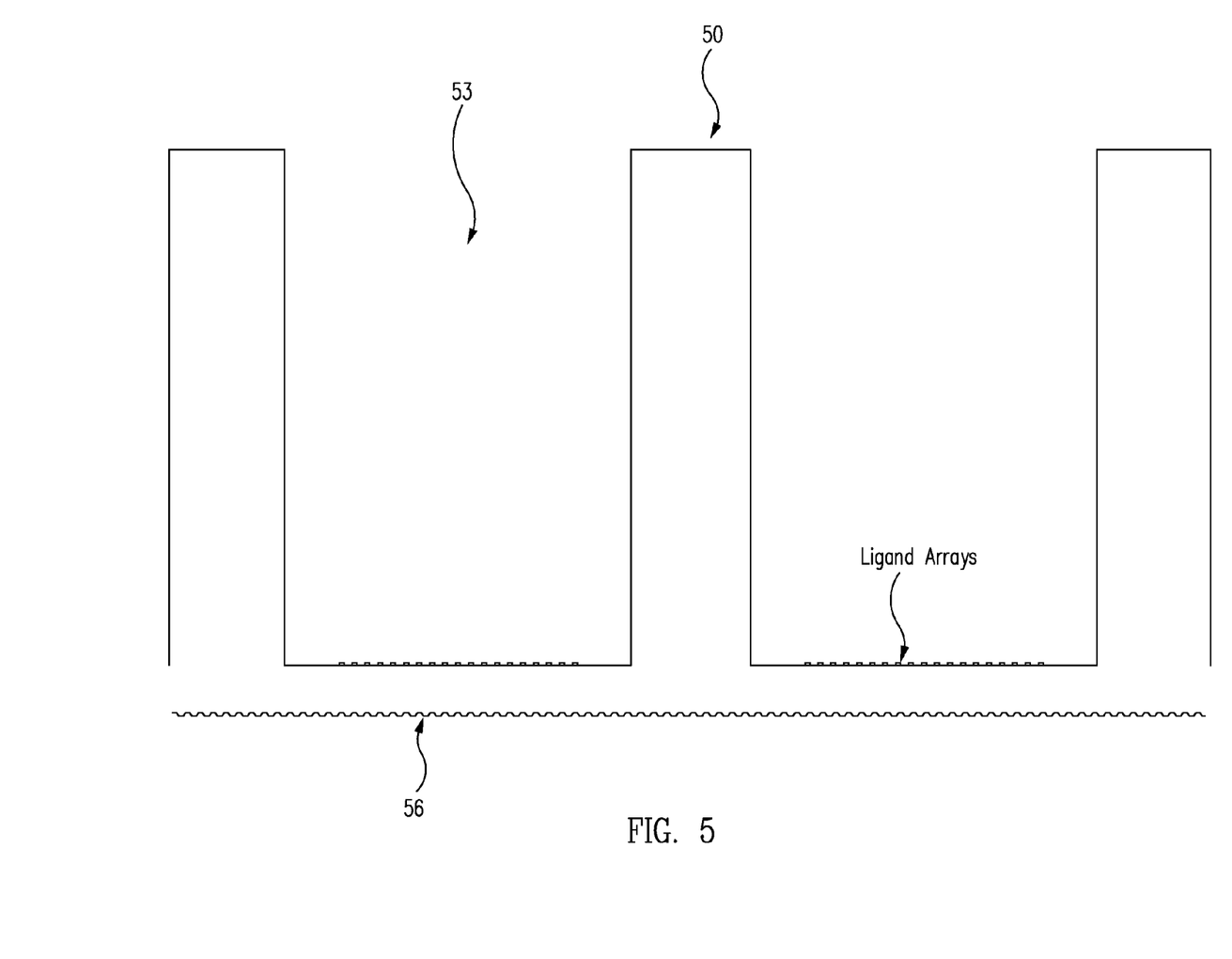
FIG. 5 illustrates a portion of a multiwell plate in accordance with another embodiment of the present invention.

In accordance with another embodiment of the present invention, FIG. 5 illustrates another plate 50 which is formed as one structure of one material to include a prism array 56 formed on a planar bottom of the plate 50 and ligand arrays formed in apertures 53 on bottom surfaces of a plurality of wells. A cover member may optionally be placed over the walls of the wells.

Figure 6:
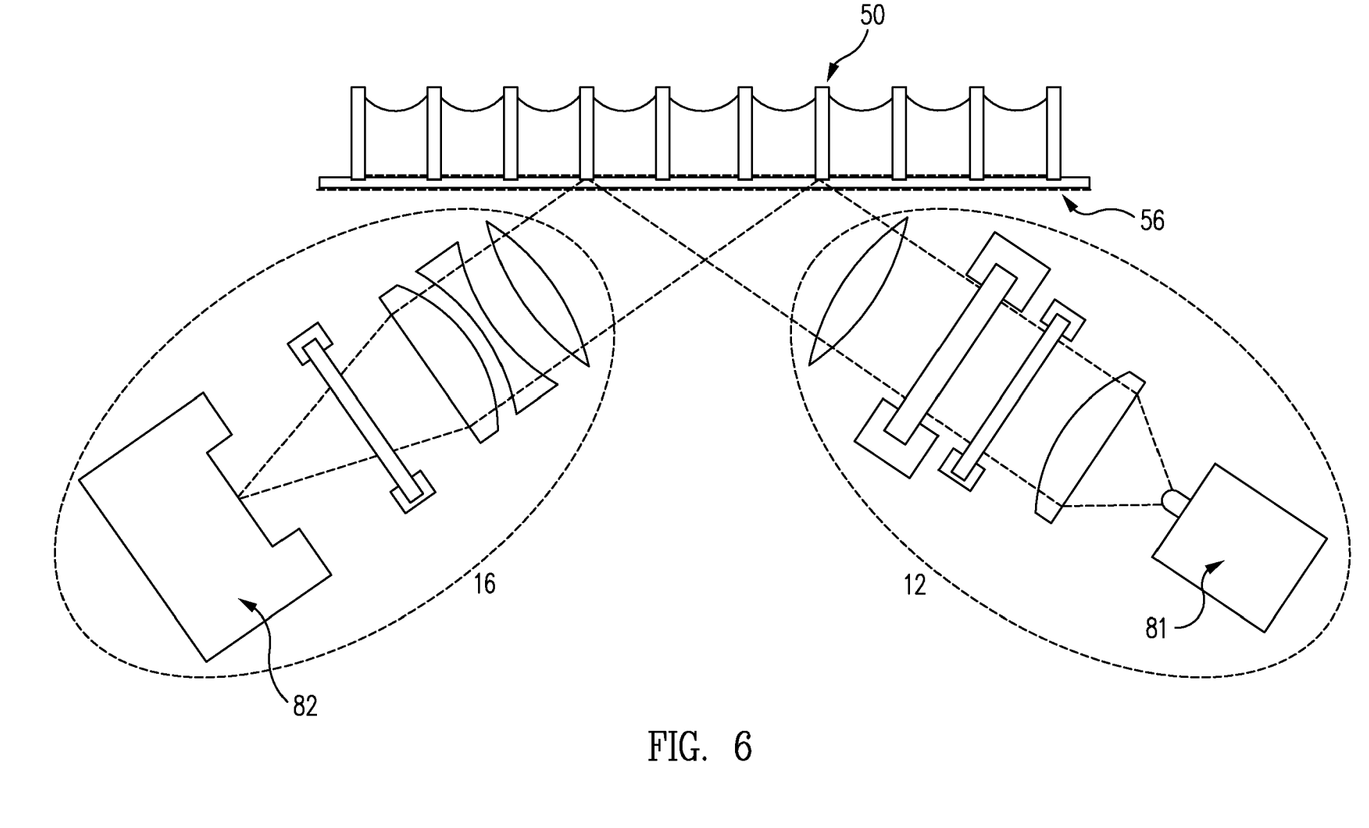

FIG. 6 shows a side view of plate 50 of FIGS. 2A-2B with an illumination subsystem 81 and an imaging subsystem 82 positioned with respect to the plate in a manner analogous to that shown for subsystems 12 and 16 in FIG. 1. In the case of FIG. 6, plate 50 encompasses the sensing subsystem. It is to be understood that subsystem 81 can be operated to illuminate individual well bottoms, a subset of well bottoms of the plate, or all the wells of the plate by well known scanning or lens arrangements. The manner of illumination and of imaging is a matter of choice and is well understood in the art.

The foregoing Detailed Description is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration those advancements, namely in accordance with the then current state of the art. It is intended that the scope of the invention be defined by the claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 USC Sec. 112, sixth paragraph, unless the element is expressly recited using the phrase "means for . . . " and no method or process step herein is to be construed under those provisions unless the step, or steps, are expressly recited using the phrase "step(s) for . . . "

What is claimed is:

1. An apparatus, comprising:
    a plate having therein a plurality of wells, each of the wells having a planar bottom surface for receiving a sample for analysis, wherein the plate has a transparent planar underside; and
    an array of prisms affixed to the underside, a plurality of prisms of the array being in registry with a corresponding one of the plurality of wells.

2. The apparatus as in claim 1, wherein the plurality of wells is arranged in rows and columns and wherein the array of prisms is formed as a continuous film.

3. The apparatus as in claim 2, wherein the continuous film comprises a layer integral with the underside of the plate.

4. The apparatus as in claim 1, wherein each prism of the array has a cross-sectional shape of a convex figure.

5. The apparatus of claim 4, wherein the convex figure includes a trapezoid.

6. The apparatus of claim 5, wherein a thickness t between the base of the plurality of prisms and the planar bottom surface of the corresponding one of the plurality of wells is given by $$t = \frac{nP\cot(\theta)}{2},$$

wherein P is a pitch of the plurality of prisms, θ is an angle of incidence of a beam of light totally internally reflected from the planar bottom surface of the corresponding one of the plurality of wells, and n is an integer.

7. The apparatus as in claim 1, wherein the array of prisms includes a uniform pattern of prisms formed in a sheet of transparent material.

8. The apparatus as in claim 7, wherein the prism sheet has a corrugated surface on one side and a smooth surface on the other, wherein the corrugated surface includes a plurality of uniform linearly arrayed prism structures.

9. The apparatus as in claim 1, wherein the array of prisms is integral with the underside of the plate.

10. The apparatus as in claim 1, further comprising a top member against a top surface of a substrate, wherein the top member has an array of through apertures exposing portions of the top surface there.

11. The apparatus as in claim 10, wherein a plurality of ligand arrays are immobilized on the top surface of a substrate at an exposed portion.

12. The apparatus of claim 1, wherein a maximum height h of the plurality of prisms is given by $$h \leq \frac{P\cot(\theta)}{2},$$

wherein P is a pitch of the plurality of prisms and θ is an angle of incidence of a beam of light totally internally reflected from the planar bottom surface of the corresponding one of the plurality of wells.

13. The apparatus of claim 1, wherein a distance x between adjacent prisms of the plurality of prisms is given by $$x \geq \frac{P(1 - \cot^2(\theta))}{2},$$

wherein P is a pitch of the plurality of prisms and θ is an angle of incidence of a beam of light totally internally reflected from the planar bottom surface of the corresponding one of the plurality of wells.

14. A system, comprising:
    a plate having therein a plurality of wells, each of the wells having a planar bottom surface including an array of immobilized ligands to receive a sample for analysis, wherein the plate has a transparent planar underside, and an array of prisms affixed to the underside, a plurality of prisms of the array being in registry with a corresponding one of the plurality of wells and with an associated array of immobilized ligands; and
    a source of a beam of light configured to direct the beam to a selected area of the array of immobilized ligands in a manner to achieve total internal reflection and to generate an evanescent field in the plane of the associated array of immobilized ligands.

15. The system as in claim 14, further comprising a sensor for sensing or measuring localized variations in the beam or beams reflected at the prisms.

16. The system as in claim 15, wherein the sensor senses or measures localized changes in intensity indicative of phase changes between the horizontal and vertical polarization vectors of a polarized beam of light responsive to the occurrence of binding between analytes in a sample in a well and ligands in an array.

17. The system as in claim 14, further comprising an optical system for directing the beam in a manner to achieve total internal reflection and to generate an evanescent field in the plane of the ligand array associated with a selected one of the prism array or position in the prism array.

18. The system as in claim 14, further comprising a sensor for sensing or measuring localized variations in the reflected beam.

19. The system as in claim 14, wherein the beam is a beam of polarized light.

20. A method of detecting binding events at an array of ligands immobilized on planar bottom surfaces of wells of a multiwell plate, the method comprising:
    transmitting a beam of polarized light to a prism film affixed to an underside surface of the plate, the prism film including a plurality of prisms in registry with a corresponding one of the wells, the prism film being of a material and geometry to permit the beam of polarized light incident thereto to be totally internally reflected in a manner to generate an evanescent field in a plane of the array of ligands at which the beam is directed; and
    obtaining an image of intensity variations in the reflected beam to detect binding events at said array of ligands.

* * * * *